(12) United States Patent
Hilser et al.

(10) Patent No.: US 7,027,969 B2
(45) Date of Patent: Apr. 11, 2006

(54) ENSEMBLE-BASED ANALYSIS OF THE PH-DEPENDENCE OF STABILITY OF PROTEINS

(75) Inventors: Vince Hilser, Galveston, TX (US); Steven T. Whitten, Dickinson, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 273 days.

(21) Appl. No.: 10/230,473

(22) Filed: Aug. 29, 2002

(65) Prior Publication Data
US 2003/0088392 A1 May 8, 2003

Related U.S. Application Data

(60) Provisional application No. 60/316,083, filed on Aug. 30, 2001.

(51) Int. Cl.
G06G 7/60 (2006.01)
G06F 19/00 (2006.01)
G11C 17/00 (2006.01)
G05B 15/00 (2006.01)

(52) U.S. Cl. ............................ 703/11; 702/19; 365/94; 700/1

(58) Field of Classification Search ................. 703/11; 702/19; 365/94; 700/1
See application file for complete search history.

(56) References Cited

U.S. PATENT DOCUMENTS 6,403,312 B1 6/2002 Dahiyat et al.

OTHER PUBLICATIONS

Lehninger Biochemistry Second Edition Worth Publishers, Inc. New York pp. 161-165 (1975).*
Murzin et al, "SCOP: A Structural Classification of Proteins Database for the Investigation of Sequences and Structures," J. Mol. Biol. (1995) 247, 536-540.
Delagrave et al, "Searching Sequence Space to Engineer Proteins: Exponential Ensemble Mutagenesis," BioTechnology vol. 11, Dec. 1993, 1548-1552.
Antosiewicz, Jan, et al.; Prediction of pH-dependent Properties of Proteins; J. Mol. Biol. (1994) 238, 415-436.
Bai, Yawen, et al.; Protein Foldling Intermediates: Native-State Hydrogen Exchange; Protein Folding Intermediates: Native-State Hydrogen Exchange; Science, vol. 269(5221), pp 192-197, Jul. 14, 1995.
Baldwin, Robert L.; Temperature dependence of the hydrophobic interaction in protein folding; Proc. Natl. Acad. Sci. USA (Biochemistry), vol. 83, pp 8069-8072, Nov. 1986.
D'Aquino, J. Alejandro, et al.; The Magnitude of the Backbone Conformational Entropy Change in Protein Folding; PROTEINS: Structure, Function, and Genetics 25:143-156 (1996).
Englander, S. Walter; Protein Folding Intermediates and Pathways Studied by Hydrogen Exchange; Annu. Rev. Biophys. Biomol. Struct. 200, 29:213-238.
Freire, Ernesto, et al.; Thermodynamics of Transfer Ribonucleic Acids: The Effect of Sodium on the Thermal Unfolding of Yeast tRNAPhe; Biopolymers, vol. 17, pp 1257-1272 (1978).
Freire, Ernesto; Statistical Thermodynamic Linkage Between Conformational and Binding Equilibria; Advances in Protein Chemistry, vol. 51, pp 255-279, 1998.
Freire, Ernesto; The propagation of binding interactions to remote sites in proteins: Analysis of the binding of the monoclonal antibody D1.3 to lysozyme; Proc. natl. Acad. Sci. USA (Biophysics), vol. 96, pp 10118-10122, Aug. 1999.
Gomez, Javier, et al.; Thermodynamic Mapping of the Inhibitor Site of the Aspartic Protease Endothiapepsin; J. Mol. Biol. (1995) 252, 337-350.
Gomez, Javier, et al.; The Heat Capacity of Proteins; PROTEINS: Structure, Function, and Genetics 22:404-412, 1995.
Habermann, Susan M., et al.; Energetics of hydrogen bonding in proteins: A model compound study; Protein Science (1996), 5:1229-1239.
Hilser, Vincent J., et al.; Structure-based Calculation of the Equilibrium Folding Pathway of Proteins. Correlation with Hydrogen Exchange Protection Factors; J. Mol. Biol. (1996) 262, 756-772.
Elcock, Adrian H.; Realistic Modeling of the Denatured States of Proteins Alloys Accurate Calculations of the pH Dependence of Protein Stability; J. Mol. Biol. (1999) 294, 1051-1062.
Hilser, Vincent J., et al.; Structure-based statistical thermodynamic analysis of T4 lysozyme mutants: structural mapping of cooperative interactions; Biophysical Chemistry 64 (1997) 69-79.
Hilser, Vincent J., et al.; The structural distribution of cooperative interactions in proteins: Analysis of the native state ensemble; Proc. Natl. Acad. Sci. USA (Biophysics), vol. 95, pp 9903-9908, Aug. 1998.
Jayaram, B., et al.; The Electrostatic Potential of B-DNA; Biopolymers, vol. 28, 975-993 (1989).
Kim, Peter S., et al.; Intermediates in the Folding Reactions of Small Proteins; Annu. Rev. Biochem. 1990, 59:631-660.
Johnson, Mark S., et al.; Alignment and Searching for Common Protein Folds Using a Data Bank of Structural Templates; J. Mol. Biol. (1993) 231, 735-752.

(Continued)

Primary Examiner—John S. Brusca
(74) Attorney, Agent, or Firm—Fulbright & Jaworski, L.L.P.

(57) ABSTRACT

The present invention relates to a computer-based algorithm that is used to determine the pKa, pH stability and electrostatic interactions of a protein.

12 Claims, 7 Drawing Sheets

OTHER PUBLICATIONS

Johannesson, Petra, et al.; Bicyclic Tripeptide Mimetics with Reverse Turn Inducing Properties; J. Med. Chem. 1999, 42, 601-608.

Klapper, Isaac, et al.; Focusing of Electric Fields in the Active Site of Cu-Zn Superoxide Dismutase: Effects of Ionic Strength and Amino-Acid Modification; PROTEINS: Structure, Function, and Genetics 1:47-59 (1986).

Kuwajima, Kunihiro; Review Article: The Molten Globule State as a Clue for Understanding the Folding and Cooperativity of Globular-Protein Structure; PROTEINS: Structure, Function, and Genetics 6:87-103 (1989).

Lee, B., et al.; The Interpretation of Protein Structures: Estimation of Static Accessibility; J. Mol. Biol. (1971) 55, 379-400.

Lee, Kon Ho, et al.; Estimation of Changes in Side Chain Configurational Entropy in Binding and Folding: General Methods and Application to Helix Formation; PROTEINS: Structure, Function, and Genetics 20:68-84 (1994).

Matthew, James B., et al.; Calculation of Electrostatic Interactions in Proteins; Methods in Enzymology, vol. 130, pp 413-436, 1986.

Matthew, James B., et al.; pH-Dependent Processes in Proteins; CRC Critical Reviews in Biochemistry, vol. 18 (2), pp 91-197, 1985.

Mayne, Leland, et al.; Two-state vs. multistate protein unfolding studied by optical melting and hydrogen exchange; Protein Science (2000), 9:1873-1877.

Milne, John S., et al.; Experimental Study of the Protein Folding Landscape: Unfolding Reactions in Cytochrome c; J. Mol. Biol. (1999) 290, 811-822.

Murphy, Kenneth P., et al.; Molecular Basis of Co-operativity in Protein Folding. III. Structural Identification of Cooperative Folding Units and Foldilng Intermediates; J. Mol. Biol. (1992) 227, 293-306.

Nozaki, Yasuhiko, et al.; Acid-Base Titrations in Concentrated Guanidine Hydrochloride. Dissociation Constants of the Guanidinium Ion and of Some Amino Acids; Journal of the American Chemical Society, 89(4): 736-742, Feb. 15, 1967.

Roxby, Robert, et al.; Hydrogen Ion Titration Curve of Lysozyme in 6 $_M$ Guanidine Hydrochloride; Biochemistry, vol. 10 (18), pp 3348-3352, 1971.

Pan, Hong, et al.; Binding sites in *Escherichia coli* dihydrofolate reductase communicate by modulating the conformational ensemble; PNAS 97 (22), pp 12020-12025, Oct. 24, 2000.

Schaefer, Michael, et al.; Electrostatic Contributions to Molecular Free Energies in Solution; Advances in Protein Chemistry, vol. 51, pp 1-57, 1998.

Shortle, David, et al.; Residual Structure in Large Fragments of Staphylococcal Nuclease: Effects of Amino Acid Substitutions; Biochemistry, 1989, 28, 936-944.

Tanford, Charles; The Interpretation of Hydrogen Ion Titration Curves of Proteins; Adv. Protein Chem. 27:69-165, 1962.

Tanford, Charles, et al.; Theory of Protein Titration Curves. I. General Equations for Impenetrable Spheres; J. Am Chem. Soc., 79 (20):5333-5339, Oct. 22, 1957.

Vita, Claudio, et al.; Novel Miniproteins Engineered by the Transfer of Active Sites to Small Natural Scaffolds; Biopolymers (Peptide Science) 47:93-100, 1998.

Warwicker, J.; Continuum Dielectric Modelling of the Protein-Solvent System, and Calculation of the Long-range Electrostatic Field of the Enzyme Phosphoglycerate Mutase; J. Theor. Biol. (1986) 121, 199-210.

Whitten, Steven T., et al.; pH Dependence of Stability of Staphylococcal Nuclease: Evidence of Substantial Electrostatic Interactions in the Denatured State; Biochemistry 2000, 39:14292-14304.

Wooll, John O., et al.; Communication: Ensemble Modulation as an Origin of Denaturant-independent Hydrogen Exchange in Proteins; J, Mol. Biol. (2000) 301:247-256.

Xie, Dong, et al.; Structure Based Prediction of Protein Folding Intermediates; J. Mol. Biol. (1994) 242, 62-80.

Xie, Dong, et al.; Molecular Basis of Cooperativity in Protein Folding. V. Thermodynamic and Structural Conditions for the Stabilization of Compact Denatured States; PROTEINS: Structure, Function, and Genetics 19:291-301 (1994).

Weißhoff, Hardy, et al.; Minicry of βII'-turns of proteins in cyclic pentapeptides with one and without D-amino acids; Eur. J. Biochem. 259, 776-788 (1999).

Tanford, Charles; Protein Denaturation; Adv. Protein Chem. 23: 121-282, 1968.

\* cited by examiner

ENSEMBLE-BASED ANALYSIS OF THE PH-DEPENDENCE OF STABILITY OF PROTEINS

This application claims priority to U.S. Provisional Application No. 60/316,083, which was filed on Aug. 30, 2001.

This invention was supported by funds obtained from the U.S. Government (National Science Foundation. Grant No. 9875689 and National Institute of Health). The U.S. Government may have certain rights in this invention.

BACKGROUND OF THE INVENTION

1. Field of the Invention

The present invention relates to the field of structural biology. More particularly, the methods of predicting pKa of a protein, the pH stability of a protein and electrostatic interactions of a protein.

2. Related Art

The solution behavior of a protein is a direct result of its chemical composition in coordination with the various conformational states it may adopt in the aqueous solvent. Enumerating these states and their free energy differences provide the information required to interpret stability, binding, allosteric effects, cooperative interactions, and function in terms of structure (Hilser et al., 1996; Hilser et al., 1997; Wooll et al., 2000; Hilser et al., 1998; Freire E., 1999; Pan et al., 2000; Freire et al., 1978; and Freire E., 1998).

Structural and energetic cataloging of states other than the "native" structure observed in crystallographic and NMR studies has proved elusive and exceedingly difficult to obtain by experiment due to the overwhelming free energy domination of the "native" state over partially folded conformers. (Kim et al., 1990; Kuwajima, 1989). But many observed protein phenomena (i.e., NMR studies on backbone dynamics; amide hydrogen exchange rates; mutational effects on binding, stability; and denaturant dependence of stability) are difficult to understand without postulating the existence and readily population of partially folded states.

Proton titration offers an ideal experimental technique for which to probe the local stability of various regions of a protein. Theoretical interpretation of proton binding curves are particularly informative because 1) protons bind non-homogeneously and to well defined sites, 2) the pKa of each binding site can be calculated directly from electrostatic theory if provided the structure (Klapper et al., 1986; Warwicker, J. 1986; Antosiewicz et al., 1994; Jayaram et al., 1989; Tanford et al., 1957; Matthew et al., 1986), and 3) the effect of proton binding on the free energy difference between the various conformational states of the ensemble is easily ascertained from linkage theory (Tanford, C 1969; Tanford, C. 1962).

A difficulty in using the above proton binding techniques is determining the ensemble of states populated at any solution pH and quantitating their structures and stabilities. The present invention is the first to address the role of partially folded states on the pH dependence of stability of proteins and how the electrostatic contribution to stability is tightly linked to structural dynamics.

BRIEF SUMMARY OF THE INVENTION

In the present invention, the COREX algorithm is used to generate an ensemble of partially folded states based on the crystallographic structure of a protein (Hilser et al., 1996).

More specifically, the present invention provides pKa values by capturing the cooperativity of proton binding, the pH dependence of stability, the role of specific titratable residues in the pH dependence of stability, and the contribution of electrostatic interactions to the overall energetics of a protein.

An embodiment of the present invention is a method of calculating the microscopic pKa of a protein comprising the steps of: inputting a high resolution structure of the protein; generating an ensemble of incrementally different conformational states by combinatorial unfolding of a set of predefined folding units in all possible combinations of the protein; determining the probability of each of said conformational state; and calculating the pH dependence of each of said conformational state. The method may further comprise predicting the residue-specific contributions to the pH dependent stability of the protein comprising the step of determining the ratio of probabilities of all microscopic states using the equation $$K_{folded,j} = \frac{P_{folded,j}}{P_{unfolded,j}}.$$

In a further embodiment, the apparent protection constant per residue is calculated using the equation $$K_{folded,j} = \frac{P_{protected,j}}{P_{exposed,j}}.$$

In specific embodiments, the generating step comprises dividing the proteins into folding units by placing a block of windows over the entire sequence of the protein and sliding the block of windows one residue at a time.

Yet further, in another specific embodiment, the determining step comprises calculating the free energy of each of the conformational states in the ensemble; determining the Boltzmann weight $[K_i = \exp(-\Delta G_i/RT)]$ of each state; and determining the probability of each state using the equation $$P_i = \frac{K_i}{\sum K_i}.$$

In another embodiment, the calculating step comprises determining the linkage relationship of the pH dependence of stability of all microscopic states using the equation $$\Delta G(pH)_i = -2.303 RT \int \Delta v(pH)_i \, dpH + \Delta G_{COREX,i}$$

In a further embodiment, the pKa is used to determine the macroscopic stability of the protein which comprises the step of determining the pH dependence of the proton binding using the equation $$Z(pH)_{ensemble} = \sum_i Z(pH)_i * P(pH)_i.$$

In another embodiment, the pKa determines the solubility of the protein.

Another embodiment of the present invention comprises a method of designing a protein pharmaceutical exhibiting increased stability comprising the steps of inputting a high resolution structure of a protein; generating an ensemble of incrementally different conformational states by combinatorial unfolding of a set of predefined folding units in all possible combinations of the protein; determining the probability of each of said conformational state; calculating the pH dependence of each of said conformational state; and designing a protein pharmaceutical with the structural characteristics found by the above steps to provided increased stability of the protein pharmaceutical.

In a specific embodiment, the protein pharmaceutical has increased stability in a basic condition. Yet further, the protein pharmaceutical has increased stability in an acidic condition.

Another embodiment is a method of designing a protein pharmaceutical exhibiting increased binding affinity between the protein pharmaceutical and a ligand comprising the steps of inputting a high resolution structure of a protein; generating an ensemble of incrementally different conformational states by combinatorial unfolding of a set of predefined folding units in all possible combinations of the protein; determining the probability of each of said conformational state; calculating the pH dependence of each of said conformational state; and designing a protein pharmaceutical with the structural characteristics found by the above steps to provide increased binding affinity of the protein pharmaceutical for the ligand.

Still yet, another embodiment is a method of designing an oral protein pharmaceutical exhibiting increased adsorption in the gastrointestinal tract comprising the steps of inputting a high resolution structure of a protein; generating an ensemble of incrementally different conformational states by combinatorial unfolding of a set of predefined folding units in all possible combinations of the protein; determining the probability of each of said conformational state; calculating the pH dependence of each said conformational state; and designing the protein pharmaceutical with the structural characteristics found by the above steps to enhance adsorption of the protein pharmaceutical in the gastrointestinal tract.

A further embodiment includes a method of calculating the macroscopic pKa of a protein comprising the steps of: generating an ensemble of incrementally different conformational states by combinatorial unfolding of a set of predefined folding units in all possible combinations of each protein; and calculating a proton binding curve of the ensemble. In specific embodiments, the binding curve is calculated using the equation $$Z(pH)_{ensemble} = \sum_i Z(pH)_i * P(pH)_i.$$

The aforementioned embodiments of the present invention may be readily implemented as a computer-based system. One embodiment of such a computer-based system includes a computer program that receives an input of high resolution structure data for one or more proteins. The computer-based program utilizes this data to determine the pKa of a protein, pH dependence of stability of proteins, and the electrostatic interactions of a protein. The data obtained from the present invention can then be stored in a database. This data can be used to design proteins having increased stability, solubility and binding affinity.

In one embodiment, the computer-based system uses a software program coupled to the above database to perform the steps of generating an ensemble of incrementally different conformational states by combinatorial unfolding of a set of predefined folding units in all possible combinations of each protein; determining the probability of each said conformational state; and calculating the pH dependence of each said conformational state.

In further embodiments, the inventive methods may be stored as computer executable instructions on computer-readable mediums.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2A shows the numerical calculation of proton titration of the ensemble (solid line); the fully folded state (large dashes); and the fully unfolded state (short dashes). FIG. 2B shows acid unfolding of wild type SNase as followed by the pH titration of intrinsic fluorescence of Trp-140 (Whitten et al., 2000).

FIG. 4A shows the residue dependence of the natural logarithm of $K_{folded}$ (black line) and $K_{protected}$ (gray line). Non-titratable residues were given a value of zero for $P_{protectedj}$. To prevent infinities in the natural log calculations, $K_{foldedj}$ was computed as $(1-P_{unfoldedj})/P_{unfoldedj}$; $K_{protectedj}$ as $(1-P_{exposedj})/P_{exposedj}$. FIG. 4B shows the effect of point mutation on the stability of SNase at pH 7 and on its pH midpoint of acid denaturation. Also shown is the predicted effect of changes in stability on the pH midpoint of acid denaturation of wild type SNase (solid line of FIG. 4B).

DETAILED DESCRIPTION OF THE INVENTION

Figure 1:
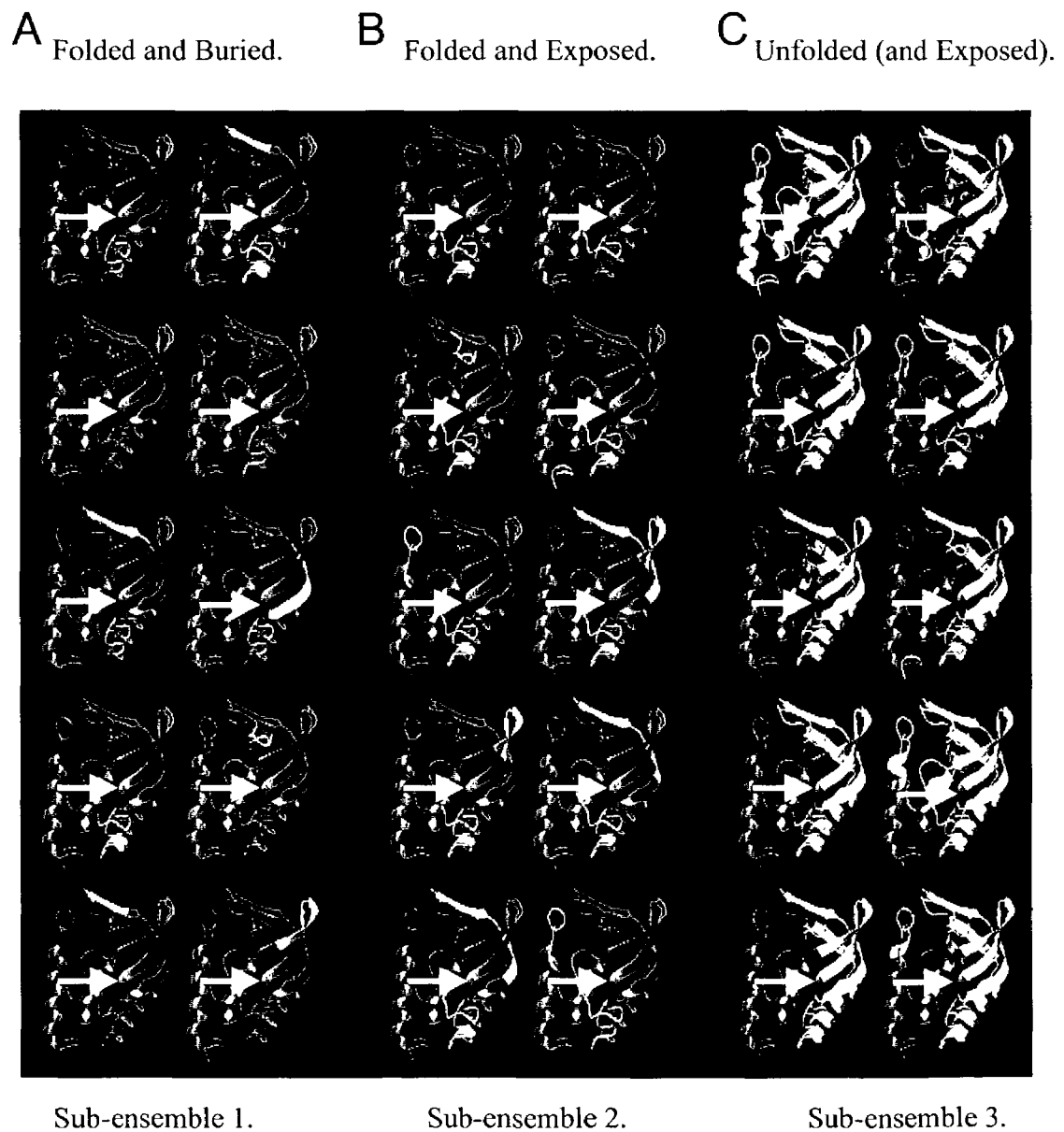
FIG. 1A–FIG. 1C show a sample of states of the ensemble that are relevant to the effect of Asp21 titration of the pH dependent stability of SNase. White arrows indicate the position of residue Asp21. Stretches of SNase having folded regions are indicated in gray; unfolded regions are indicated in white. The first sub-ensemble (FIG. 1A) is a sample of the states in which Asp21 resides in a region of the protein that is folded and protected from solvent. The second sub-ensemble (FIG. 1B) consists of some of the states where Asp21 is folded but exposed to the solvent. The third sub-ensemble (FIG. 1C) is representative of states where Asp21 is unfolded and thus exposed to solvent.

It is readily apparent to one skilled in the art that various embodiments and modifications may be made to the invention disclosed in this Application without departing from the scope and spirit of the invention.

As used herein the specification, "a" or "an" may mean one or more. As used herein in the claim(s), when used in conjunction with the word "comprising", the words "a" or "an" may mean one or more than one. As used herein "another" may mean at least a second or more.

Aggregation, as used herein, refers to the interaction of proteins, usually non-specific, to form a complex that may or may not be covalently linked.

Another, as used herein, may mean at least a second or more.

Autologous protein, polypeptide or peptide, as used herein, refers to a protein, polypeptide or peptide which is derived or obtained from an organism.

Based upon a tertiary structure, as used herein, refers to a structure that possesses a similar backbone structure to that of the original structure that it is referred to being based upon.

Configuration, as used herein, refers to different conformations of a protein molecule that have the same chirality of atoms.

Conformation, as used herein, refers to various nonsuperimposable three-dimensional arrangements of atoms that are interconvertible without breaking covalent bonds.

Computer modeling, as used herein, refers to the construction of patterns using raw data to simulate an object or the interaction of objects using a computer. For example, computer modeling is used to determine the size, shape, and interaction of certain compounds in order to develop treatments associated to a specific disease.

Computer simulation, as used herein, refers to a software program that runs on any size computer that attempts to simulate some phenomenon based on a scientist's conceptual and mathematical understanding of the phenomenon. The scientist's conceptual understanding is reduced to an algorithmic or mathematical logic, which is then programmed in one of many programming languages and compiled to produce a binary code that runs on a computer. Also, the act of running such a code on a computer.

Database, as used herein, refers to any compilation of information regarding the relation of experimental and analytical data of a protein. The database used may be publicly available, commercially available or one created by the inventors. An example of a publicly available database is the Protein Data Bank.

Generate or generating, as used herein, refers the act of defining or originating by the use of one or more operations. Skilled artisans using the invention may create the matter or data themselves or locate the matter or data elsewhere and utilize it in the practice of the invention. One skilled in the art realizes that in this invention all of the test data or experimental data may be obtained commercially or publicly or generated by procedures and techniques defined herein. The terms "generating" and "obtaining" are mutually inclusive as used herein.

Ligand, as used herein, refers to a proteinaceous or non-proteinaceous compound. The ligand may be, but is not limited to, a receptor, an enzyme, a coenzyme, or a non-proteinaceous chemical compound.

Loop, as used herein, are turns in the polypeptide chain that reverse the direction of the polypeptide chain at the surface of the molecule.

Macroscopic, as used herein, refers to a state of being generated from experimental procedures. For example, but not limited to, the macroscopic stability of a protein refers to the stability of the protein which was generated from experimental procedures. Experimental procedures may also be referred to as "wet science".

Micriscopic, as used herein, refers to a state of being generated from structure-based calculations. For example, but not limited to, the microscopic stability of a protein refers to the stability of the protein which was calculated from a three-dimensional structure using various techniques, however, experimental procedures were not used. Structure-based calculations can be referred to as "dry science".

Peptide, as used herein, refers to a chain of amino acids with a defined sequence whose physical properties are those expected from the sum of its amino acid residues and there is no fixed three-dimensional structure.

Pharmaceutical properties, as used herein, refer to, but are not limited to, binding affinity, aggregation, solubility, and immunogenic effects.

Protein, as used herein, refers to a chain of amino acid residues usually of defined sequence, length and three dimensional structure. The polymerization reaction which produces a protein results in the loss of one molecule of water from each amino acid, proteins are often said to be composed of amino acid residues. Natural protein molecules may contain as many as 20 different types of amino acid residues, each of which contains a distinctive side chain. A protein may be composed of multiple peptides.

Protein fold as used herein refers to an organization of a protein to form a structure which constrains individual amino acids to a specific location relative to the other amino acids in the sequence. One of skill in the art realizes that this type of organization of a protein comprises secondary, tertiary and quaternary structures.

Solubility, as used herein, refers to the amount of the protein that can be dissolved in a given volume of a solvent.

Variant, as used herein, refers to a protein with a given set of mutation(s).

One of skill in the art is cognizant that the properties of proteins are governed by their potential energy surfaces. Proteins exist in a dynamic equilibrium between a folded, ordered state and an unfolded, disordered state. This equilibrium in part reflects the interactions between the side chains of amino acid residues which tend to stabilize the protein's structure, and, on the other hand, those thermodynamic forces which tend to promote the randomization of the molecule.

There is a hierarchy of protein structure. The primary structure is the covalent structure which comprises the particular sequence of amino acid residues in a protein and any posttranslational covalent modifications that may occur. The secondary structure is the local conformation of the polypeptide backbone. The helices, sheets and turns of a protein's secondary structure pack together to produce the three-dimensional structure of the protein. The three-dimensional structure of many proteins may be characterized as having internal surfaces (directed away from the aqueous environment in which the protein is normally found) and external surfaces (which are in close proximity to the aqueous environment). Through the study of many natural proteins, researchers have discovered that hydrophobic residues (such as tryptophan, phenylalanine, tyrosine, leucine, isoleucine, valine or methionine) are most frequently found on the internal surface of protein molecules. In contrast, hydrophilic residues (such as asparate, asparagine, glutamate, glutamine, lysine, arginine, histidine, serine, threonine, glycine, and proline) are most frequently found on the external protein surface. The amino acids alanine, glycine, serine and threonine are encountered with equal frequency on both the internal and external protein surfaces.

I. Determination of pKa

In the present invention, the COREX algorithm is used to generate an ensemble of partially folded states based on the crystallographic structure of protein (Hilser et al., 1996). The crystallographic structure of a protein or NMR structure can be retrieved from a database that is well known and used by those of skill in the art. One such database is the Protein Data Bank.

The pKa values of the present invention are provided by capturing the cooperativity of proton binding, the pH dependence of stability, the role of specific titratable residues in the pH dependence of stability, and the contribution of electrostatic interactions to the overall energetics of a protein. The proton binding properties of each state within the ensemble, including the fully folded and fully unfolded conformers, was calculated using pKa values derived from structure-based Finite Difference solution of the linearized Possion-Boltzmann equation. The equilibrium population distribution of states of the ensemble was determined by empirical parameterization of the intrinsic energetics ($\Delta G$, $\Delta H$, and $\Delta S$) of each state through solvent accessible surface area calculations. The effect of pH on the equilibrium population distribution was determined with linkage relationships by calculating the difference in proton binding between the states.

A. Microscopic Behavior

In specific embodiments, the method of calculating the microscopic pKa of a protein comprises the steps of inputting a high resolution structure of the protein; generating an ensemble of incrementally different conformational states by combinatorial unfolding of a set of predefined folding units in all possible combinations of the protein; determining the probability of each of said conformational states; and calculating the pH dependence of each of the said conformational states The present invention utilizes a computational method comprising the step of determining a stability constant from the ratio of the summed probability of all states in the ensemble in which a residue j is in a folded conformation to the summed probability of all states in which j is in an unfolded conformation according the equation, $$K_{f,j} = \frac{\sum Pfolded,j}{\sum Punfolded,j}$$

The probability that a given residue j is in the folded conformation, $P_{folded,j}$, is equal to the sum of the probabilities of all the conformational states of the protein in which residue j resides in a folded region. Likewise, the probability that residue j is unfolded, $P_{unfolded,j}$, is equal to the sum of the probabilities of all the conformational states of the protein in which residue j resides in an unfolded region. The apparent folding constant per residue, $K_{folded,j}$, is thus defined as the ratio of probabilities of all states in which residue j is folded to the probabilities of the states in which residue j is not folded.

One of skill in the art realizes that an important aspect of the theoretical approach presented herein is the ability to query the contribution of each titratable residue to the pH dependent stability of the protein. Thus, all residues may not equally affect stability upon titration. It is contemplated that some titratable groups are fully exposed to solvent, thus contributing to stability mainly through solubility concerns. Yet further, it is contemplated that any possible intramolecular coulombic interactions are attenuated by the ionic and polar components of the solvent. Also, other titratable groups may participate in substantial intramolecular coulombic interactions, minimally attenuated by the solvent, and contribute substantially to the electrostatic and proton-linked components of protein stability.

Yet further, an apparent protection constant per residue, $K_{protected,j}$, can be defined as the ratio of the sum of probabilities of all states in which the titratable atom of residue j is protected from the solvent to the sum of the probabilities of all states in which the titratable atom of residue j is exposed.

$$K_{folded,j} = \frac{P_{protected,j}}{P_{exposed,j}}$$

It is contemplated that residues that reside in regions of the protein with little probability of being folded will not contribute to the pH dependent stability even if they possess pKa shifted from $pKa_{exposed}$ values and are well protected from the solvent in the fully folded state.

In specific embodiments, the generating step comprises dividing the proteins into folding units by placing a block of windows over the entire sequence of the protein and sliding the block of windows one residue at a time.

One of skill in the art is cognizant that the division of a protein into a given number of folding units is a partition. Thus, to maximize the number of partially folded states, different partitions are used in the analysis. The partitions can be defined by placing a block of windows over the entire sequence of the protein. The folding units are defined by the location of the windows irrespective of whether they coincide with specific secondary structure elements. By sliding the entire block of windows one residue at a time, different partitions of the protein are obtained. For two consecutive partitions, the first and last amino acids of each folding unit are shifted by one residue. This procedure is repeated until the entire set of partitions has been exhausted. In specific embodiments, windows of 5 or 8 amino acid residues are used. One of skill in the art realizes that approximately $10^5$ partially folded conformations can be generated using the COREX algorithm. This value can be altered by increasing or decreasing the window size and the size of the protein.

One of skill in the art is aware that the COREX algorithm generates a large number of partially folded states of a protein from the high resolution crystallographic or NMR structure (Hilser & Freire, 1996; Hilser & Freire, 1997 and Hilser et al., 1997). In this algorithm, the high resolution structure is used as a template to approximate the ensemble of partially folded states of a protein. Thus, the protein is considered to be composed of different folding units. The partially folded states are generated by folding and unfolding these units in all possible combinations. There are two basic assumptions in the COREX algorithm: (1) the folded regions in partially folded states are native-like; and (2) the unfolded regions are assumed to be devoid of structure or lacking structure. Thermodynamic quantities, i.e., $\Delta H$, $\Delta S$, $\Delta Cp$, and $\Delta G$, partition function and probability of each state ($P_i$) are evaluated using an empirical parameterization of the energetics (Murphy & Freire, 1992; Gomez et al., 1995; Hilser et al., 1996; Lee et al., 1994; D'Aquino et al., 1996; and Luque et al., 1996).

Protein folds can be considered as one of the most basic molecular parts. A skilled artisan recognizes that the properties related to protein folds can be divided into two parts, intrinsic and extrinsic. The intrinsic properties relates to an individual fold, e.g., its sequence, three-dimensional structure and function. Extrinsic properties relates to a fold in the context of all other folds, e.g., its occurrence in many genomes and expression level in relation to that for other folds.

In further embodiments, the determining step comprises determining the free energy of each of the conformational states in the ensemble; determining the Boltzmann weight $[K_i=\exp(-\Delta G_i/RT)]$ of each state; and determining the probability of each state using the equation, $$P_i = \frac{K_i}{\sum K_i'}$$

In another embodiment, the calculating step comprises determining the linkage relationship of the pH dependence of stability of all microscopic states using the equation $\Delta G(pH)_i = -2.303RT\int \Delta v(pH)_i dpH + \Delta G_{COREX,i}$. The $\Delta G_{pH,i}$ is the pH dependence of stability of state i relative to the "native" crystallographic structure (N), R is the gas constant, T is temperature, $\Delta v_{pH,i}$ is the difference in proton binding between state i and N as a function of pH, and $\Delta G_{COREX,i}$ is the stability of state i determined by empirical parameterization of the intrinsic energetics ($\Delta G$, $\Delta H$, and $\Delta S$) through solvent accessible surface area calculations. One of skill in the art realizes that the $\Delta G_{pH,i}$ equation demonstrates that an increase in proton concentration has an effect of stabilizing the states of the ensemble that possess higher affinities for protons. Thus, microscopic behavior determines the contribution of each titratable residue to the pH dependent stability of the protein.

Thus, from the above equations, one skilled in the art realizes that the COREX algorithm can be used to determine the pKa of a protein. It is well known by those of skill in the art that the pKa is the negative logarithm of Ka.

Ka=[H+][A-]/[[HA]

pKa=-log Ka

Yet further, a skilled artisan is aware that by taking the negative logarithm of both sides of the above equation, that one obtains the Henderson-Hasselbalch equation:

pH=pKa+log {[A-]/[[HA]}

Thus, it is well known that the pH of a substance relates to the [conjugate base]/[acid] ratio. Yet further, the Henderson-Hasselbalch equation may be used to describe the course of titration of a weak acid.

Yet further, one skilled in the art realizes that the present invention can be used to determine how charges affect the distribution of states in the ensemble and thus the macroscopic stability of proteins.

One of skill in the art realizes that pH induced shifts in the ensemble of population of states are seen in the pH dependence of proton binding. A proton binding curve of the ensemble can be determined by the following equation:

$$Z(pH)_{ensemble} = \sum_i Z(pH)_i * P(pH)_i$$

$Z(pH)_i$ is the number of protons bound to state $i$, $P_i$ from equation $$P_i = \frac{\exp\left(\frac{-\Delta G_i}{RT}\right)}{Q}$$

II. Protein Design

Another embodiment of the present invention is the design of proteins to enhance the pharmaceutical or industrial uses of the protein. For example, a skilled artisan may desire to produce proteins having increased protein stability, which translates into longer shelf life and increased activity under less than optimal conditions.

Thus, in specific embodiments, the present invention comprises a method of designing a protein pharmaceutical exhibiting increased stability comprising the steps of inputting a high resolution structure of a protein; generating an ensemble of incrementally different conformational states by combinatorial unfolding of a set of predefined folding units in all possible combinations of the protein; determining the probability of each of said conformational state; calculating the pH dependence of each of said conformational state; and designing a protein pharmaceutical with the structural characteristics found by the above steps to provide increased stability of the protein pharmaceutical. Increased stability can include increased solubility or decreased aggregation of the protein.

Another embodiment is a method of designing an oral protein pharmaceutical exhibiting increased adsorption in the gastrointestinal tract comprising the steps of inputting high resolution structure of a protein; generating an ensemble of incrementally different conformational states by combinatorial unfolding of a set of predefined folding units in all possible combinations of each protein; determining the probability of each said conformational state; calculating the pH dependence of each said conformational state; and designing the protein pharmaceutical with the structural characteristics found by the above steps to enhance adsorption of the protein pharmaceutical in the gastrointestinal tract.

Also, the present invention can be used to design proteins that are more stable in acid conditions, thereby making them more resistant to acid denaturation. This is especially useful for pharmaceutical formulation where long term storage results in increased acidification of suspensions and solutions.

Yet further, the present invention can be used to design proteins that are more susceptible to acid denaturation conditions, thereby making them more amenable to membrane adsorption in the acidic conditions of the gastrointestinal tract.

In designing protein pharmaceuticals, the present invention can also use rational drug design to design protein pharmaceuticals that have the desired properties. The goal of rational drug design is to produce structural analogs of biologically active compounds. By creating such analogs, it is possible to fashion drugs which are more active or stable than the natural molecules, which have different susceptibility to alteration or which may affect the function of various other molecules. In one approach, one would generate a three-dimensional structure for the protein or a fragment thereof. This could be accomplished by X-ray crystallography, computer modeling or by a combination of both approaches. An alternative approach involves the random replacement of functional groups throughout the protein, and the resulting affect on function determined.

It also is possible to isolate a protein specific antibody, selected by a functional assay, and then solve its crystal structure. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using an antibody as the antigen.

Thus, one may design drugs which have enhanced and improved biological activity for a given condition relative to a starting structure of the protein. In addition, knowledge of the chemical characteristics of these compounds permits computer employed predictions of structure-function relationships.

It is also contemplated that structurally similar compounds may be formulated to mimic the key portions of peptide or polypeptides. Such compounds are not termed peptidomimetics. Certain mimetics that mimic elements of protein secondary and tertiary structure are described in Johnson et al. (1993). The underlying rationale behind the use of peptide mimetics is that the peptide backbone of proteins exists chiefly to orient amino acid side chains in such a way as to facilitate molecular interactions, such as those of antibody and/or antigen. A peptide mimetic is thus designed to permit molecular interactions similar to the natural molecule.

Some successful applications of the peptide mimetic concept have focused on mimetics of beta-turns within proteins, which are known to be highly antigenic. Likely beta-turn structure within a polypeptide can be predicted by computer-based algorithms. Once the component amino acids of the turn are determined, mimetics can be constructed to achieve a similar spatial orientation of the essential elements of the amino acid side chains.

Other approaches have focused on the use of small, multidisulfide-containing proteins as attractive structural templates for producing biologically active conformations that mimic the binding sites of large proteins (Vita et al., 1998). A structural motif that appears to be evolutionarily conserved in certain toxins is small (30–40 amino acids), stable, and high permissive for mutation. This motif is composed of a beta sheet and an alpha helix bridged in the interior core by three disulfides.

Beta II turns have been mimicked successfully using cyclic L-pentapeptides and those with D-amino acids. Weisshoff et al. (1999). Also, Johannesson et al. (1999) report on bicyclic tripeptides with reverse turn inducing properties.

Methods for generating specific structures have been disclosed in the art. For example, alpha-helix mimetics are disclosed in U.S. Pat. Nos. 5,446,128; 5,710,245; 5,840,833; and 5,859,184. Theses structures render the peptide or protein more thermally stable, also increase resistance to proteolytic degradation. Six, seven, eleven, twelve, thirteen and fourteen membered ring structures are disclosed.

Methods for generating conformationally restricted beta turns and beta bulges are described, for example, in U.S. Pat. Nos. 5,440,013; 5,618,914; and 5,670,155. Beta-turns permit changed side substituents without having changes in corresponding backbone conformation, and have appropriate termini for incorporation into peptides by standard synthesis procedures. Other types of mimetic turns include reverse and gamma turns. Reverse turn mimetics are disclosed in U.S. Pat. Nos. 5,475,085 and 5,929,237, and gamma turn mimetics are described in U.S. Pat. Nos. 5,672,681 and 5,674,976.

A. Proteins with Increased Solubility

In another embodiment, the present invention can be used to determine how charges affect the distribution of states in the ensemble, and thus the solubility of the protein. Thus, the present invention is especially useful for determining surface charge groups. It is contemplated that upon determining how the charges affect the distribution of the states of the ensemble, a protein pharmaceutical may be designed by substituting amino acids to alter the charge and increase the solubility of the protein.

The solubility of a protein is the amount of the protein that can be dissolved in a given volume of a solvent. The presence of greater than this amount of the protein will cause the protein to aggregate and precipitate. The solubility of a protein in water is determined by its free energy when surrounded by aqueous solvent relative to its free energy when interacting in an amorphous or ordered solid state with any other molecules that might be present, or when immersed in membranes. A factor in the solubility of any substance is the amount of energy required to displace the buffer to accommodate the substance. Ionic strength, pH and temperature of the buffer affect the solubility of a protein. Increasing the ionic strength of the buffer at low values tends to increase solubility of the protein, while increasing ionic strength at high values tends to decrease solubility. In a low ionic strength buffer, the protein is surrounded by an excess of ions of charge opposite to the net charge of the protein. This decreases the electrostatic free energy of the protein and increases solubility. In an aqueous solvent, charged and polar groups on the surface of the protein interact favorably with water. Organic solvents tend to decrease the solubility of proteins. A protein is least soluble at its isoelectric point. At a pH above the isoelectric point, the protein is deprotonated and soluble. At a pH below the isoelectric point, the protein is protonated and soluble. The greater the net charge on a protein, the more likely they are to stay in solution. This is due to the greater electrostatic repulsions between molecules. High temperature causes proteins to denature, thus aggregating and losing solubility.

Thus, one skilled in the art realizes that amino acid substitutions can be based on the amino acid side-chain substituents, for example, their hydrophobicity, hydrophilicity, charge, size, and/or the like. An analysis of the size, shape and/or type of the amino acid side-chain substituents reveals that arginine, lysine and/or histidine are all positively charged residues; that alanine, glycine and/or serine are all a similar size; and/or that phenylalanine, tryptophan and/or tyrosine all have a generally similar shape.

To effect more quantitative changes, the hydropathic index of amino acids may be considered. Each amino acid has been assigned a hydropathic index on the basis of their hydrophobicity and/or charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and/or arginine (−4.5).

The importance of the hydropathic amino acid index in conferring interactive biological function on a protein is generally understood in the art (Kyte & Doolittle, 1982, incorporated herein by reference). It is known that certain amino acids may be substituted for other amino acids having a similar hydropathic index and/or score and/or still retain a similar biological activity. In making changes based upon the hydropathic index, the substitution of amino acids whose hydropathic indices are within ±2 is preferred, those which are within ±1 are particularly preferred, and/or those within ±0.5 are even more particularly preferred.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with its immunogenicity and/or antigenicity, i.e., with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In making changes based upon similar hydrophilicity values, the substitution of amino acids whose hydrophilicity values are within ±2 is preferred, those which are within ±1 are particularly preferred, and/or those within ±0.5 are even more particularly preferred.

In making modifications, the polarity of amino acid residues may be considered. Polar amino acid residues may include: lysine, arginine, histidine, aspartic acid, glutamic acid, asparagine, glutamine, serine, threonine, and tyrosine. Nonpolar amino acid residues may include: alanine, glycine, valine, leucine, isoleucine, proline, phenylalanine, methionine, tryptophan, and cysteine (Alberts et al., 1994).

B. Proteins Having Increased Binding Affinity

In further embodiments, the present invention can be used to determine how charges affect the distribution of states in the ensemble, and thus can be used as an additional means of stabilizing binding competent states, which will ultimately result in increased affinity of the protein for its putative target.

Thus, the present invention may be used to design a protein pharmaceutical exhibiting increased binding affinity between the protein pharmaceutical and a ligand. The method of designing the protein pharmaceutical may comprise the steps of inputting high resolution structure of a protein; generating an ensemble of incrementally different conformational states by combinatorial unfolding of a set of predefined folding units in all possible combinations of the protein; determining the probability of each of said conformational state; calculating the pH dependence of each said conformational state; and designing a protein pharmaceutical with the structural characteristics found by the above steps to provide increased binding affinity of the protein pharmaceutical for the ligand.

Binding affinity is the measure of the overall free energy of the interaction between the protein and the ligand. The magnitude of the affinity determines whether a particular interaction is relevant under a given set of conditions. Whether or not any particular affinity of a protein for a ligand is significant depends on the concentration of the ligand present for the protein to encounter. Assays for determining binding affinity include, but are not limited to, surface plasmon resonance, Western blot, ELISA, DNase footprinting, and gel mobility shift assays. The ligand may be protein or non-protein. The ligand may be, but is not limited to, a receptor, a coenzyme, or a non-proteinaceous chemical compound. Binding affinity between a protein and ligand may be measured by the association or dissociation constant of the binding between the protein and the ligand. Entropy of binding between the protein and ligand may be decreased by stabilizing structures similar to that of the protein in a bound state with the ligand. van der Waals calculations can be performed with the protein and the ligand to determine whether binding conformation will be sterically allowed.

C. Other Protein Designs

The invention can also be used to study the underlying origins of functional changes caused by polymorphic charge variations in both human and animals. Yet further, the present invention can be used to study the underlying origins of functional changes caused by polymorphic variations that affect charge residues in both human and animals.

One skilled in the art is cognizant that a polymorphism may occur at the genomic level of a species resulting in an amino acid change. For example, a positive charged amino acid may be replaced by a negative charged amino acid. Yet further, a non-charged or neutral amino acid may be replaced by a charged amino acid. Thus, a skilled artisan realizes that a polymorphism may result in a change in the overall charge of the protein. This polymorphic variation can be in the protein backbone or in a functional group of the protein.

Yet further, the present invention can be used to design proteins that are more stable in basic conditions, thereby making them more resistant to base denaturation. This is especially useful for detergents that incorporate proteases.

In still another embodiment, the present invention can be used to identify functionally important residues on a virus that act as pH dependent triggers for activation.

In another embodiment, the present invention can be used in conjunction with current electrostatics packages contained in programs like DELPHI which provide researchers with valuable tools for studying effects of pH and charge/charge interactions on a wide range of biophysical properties. Thus, this algorithm is a useful addition to existing research tools.

The aforementioned embodiments of the present invention may be readily implemented as a computer-based system. One embodiment of such a computer-based system includes a computer program that receives an input of high resolution structure data for one or more proteins. The computer-based program utilizes this data to determine the pKa of a protein, pH dependence of stability of proteins, and the electrostatic interactions of a protein. The data obtained from the present invention can then be stored in a database. This data can be used to design a proteins having increased stability, solubility and binding affinity.

In one embodiment, the computer-based system uses a software program coupled to the above database to perform the steps of generating an ensemble of incrementally different conformational states by combinatorial unfolding of a set of predefined folding units in all possible combinations of each protein; determining the probability of each said conformational state; and calculating the pH dependence of each said conformational state.

In further embodiments, the inventive methods may be stored as computer executable instructions on computer-readable mediums.

IV. EXAMPLES

The following examples are included to demonstrate preferred embodiments of the invention. It should be appreciated by those skilled in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention.

Example 1

Ensemble Computational Details

The crystallographic structure of a protien was used as a template to computationally generate an ensemble of partially folded states using the COREX algorithm. A window size of at least 5 was used, generating partially folded states. The equilibrium population distribution of states of the ensemble, including the fully folded and fully unfolded conformers, was determined by empirical parameterization of the intrinsic energetics ($\Delta G$, $\Delta H$, and $\Delta S$) of each state through solvent accessible surface area calculation (Hilser et al., 1996; Murphy et al., 1992; D'Aquino et al., 1996; Gomez et al., 1995; Xie et al., 1994) and equations 1 and 2, as shown below.

Briefly, COREX generated an ensemble of partially unfolded microstates using the high-resolution structure of each protein as a template (Hilser & Freire, 1996). This was facilitated by combinatorially unfolding a predefined set of folding units (i.e., residues 1–5 are in the first folding unit, residues 6–10 are in the second folding unit, etc.). By means of an incremental shift in the boundaries of the folding units, an exhaustive enumeration of the partially unfolded species was achieved for a given folding unit size.

For each microstate i in the ensemble, the Gibbs free energy was calculated from the surface area-based parameterization described previously (D'Aquino, 1996; Gomez, 1995; Xie, 1994; Baldwin, 1986; Lee, 1994; Habermann, 1996). The Boltzmann weight of each microstate [i.e., $K_i = \exp(-\Delta G_i/RT)$] was used to calculate its probability:

$$P_i = \frac{K_i}{\sum K_i} \quad (1)$$

where the summation in the denominator is over all microstates. From the probabilities calculated in Equation 1, an important statistical descriptor of the equilibrium was evaluated for each residue in the protein. Defined as the residue stability constant, $\kappa_{f,j}$, this quantity was the ratio of the summed probability of all states in the ensemble in which a particular residue j was in a folded conformation ($\Sigma P_{f,j}$) to the summed probability of all states in which j was in an unfolded conformation ($\Sigma P_{nf,j}$):

$$\kappa_{f,j} = \frac{\sum P_{f,j}}{\sum P_{nf,j}} \quad (2)$$

The Gibbs energy for each microstate i relative to the fully folded structure was calculated the below equation:

$$\Delta G_i = \Delta H_i, \text{solvation} - T(\Delta S_i, \text{solvation} + W \Delta S_i, \text{conformational}) \quad (3)$$

where the calorimetric enthalpy and entropy of solvation were parameterized from polar and a polar surface exposure, and the conformational entropy was determined (Hilser & Freire, 1996).

Example 2

Prediction of Proton Binding Properties

The crystallographic structure of SNase (1stn.pdb) was used as a template to computationally generate an ensemble of partially folded states using the COREX algorithm (Hilser et al., 1996). A window size of 8 was used, generating 1179629 partially folded states. The equilibrium population distribution of states of the ensemble, including the fully folded and fully unfolded conformers, was determined by empirical parameterization of the intrinsic energetics ($\Delta G$, $\Delta H$, and $\Delta S$) of each state through solvent accessible surface area calculations (Hilser et al., 1996).

The proton binding properties of each state within the ensemble was determined using structure-based pKa calculations on the crystallographic structure. Briefly, four different calculations were used on the crystallographic structure of SNase: 1) Finite Difference (FD) method with solution to the linear Poisson-Boltzman (PB) equation (Antosiewicz et al., 1994), 2) FD method with solution to the non-linear PB equation (Jayaram et al., 1989), 3) Tanford-Kirkwood (TK) method (Tanford et al., 1957), and 4) a simple axiomatic method where if the titratable atom of a residue is exposed to solvent, then the residue titrates with the same pKa as solvent exposed model compounds, (i.e. the atom is protected from solvent). If the residue titrated with a pKa shifted by 3 pK units (down for acidic residues, up for basic residues) then it was indicative of a local electrostatic environment favorable to charge. Results of these calculations were illustrated in Table 1 as shown below.

TABLE 1 pK_a values used in calculations.

| Residue | pK$_{a,protected}$[1] | pK$_{a,exposed}$[2] | pK$_{a,GuHCl}$[3] |
|---|---|---|---|
| Nterm* | 7.40 | 7.40 | 7.60 |
| Cterm* | 3.50 | 3.50 | 3.40 |
| Glu10 | 2.573 | 4.50 | 4.38 |
| Glu43 | 5.086 | 4.50 | 4.38 |
| Glu52 | 2.127 | 4.50 | 4.38 |
| Glu57 | 3.673 | 4.50 | 4.38 |
| Glu67 | 2.894 | 4.50 | 4.38 |
| Glu73 | 3.698 | 4.50 | 4.38 |
| Glu75 | 1.286 | 4.50 | 4.38 |
| Glu101 | 2.25 | 4.50 | 4.38 |
| Glu122 | 2.851 | 4.50 | 4.38 |
| Glu129 | 1.213 | 4.50 | 4.38 |
| Glu135 | 3.303 | 4.50 | 4.38 |
| Glu142* | 4.50 | 4.50 | 4.38 |
| Asp19 | 2.465 | 4.00 | 3.88 |
| Asp21 | 0.524 | 4.00 | 3.88 |
| Asp40 | 2.077 | 4.00 | 3.88 |
| Asp77 | 2.36 | 4.00 | 3.88 |
| Asp83 | 1.327 | 4.00 | 3.88 |
| Asp95 | 2.503 | 4.00 | 3.88 |
| Asp143* | 4.00 | 4.00 | 3.88 |
| Asp146* | 4.00 | 4.00 | 3.88 |
| His8 | 6.347 | 6.50 | 6.83 |
| His46 | 5.429 | 6.50 | 6.83 |
| His121 | 5.183 | 6.50 | 6.83 |
| His124 | 5.957 | 6.50 | 6.83 |
| Lys5* | 10.40 | 10.40 | 10.60 |
| Lys6 | 10.437 | 10.40 | 10.60 |
| Lys16 | 9.974 | 10.40 | 10.60 |
| Lys24 | 10.238 | 10.40 | 10.60 |
| Lys28 | 10.995 | 10.40 | 10.60 |
| Lys45 | 11.547 | 10.40 | 10.60 |
| Lys48 | 10.556 | 10.40 | 10.60 |
| Lys49 | 11.348 | 10.40 | 10.60 |
| Lys53 | 11.771 | 10.40 | 10.60 |
| Lys63 | 11.482 | 10.40 | 10.60 |
| Lys64 | 10.771 | 10.40 | 10.60 |
| Lys70 | 10.656 | 10.40 | 10.60 |
| Lys71 | 10.775 | 10.40 | 10.60 |
| Lys78 | 10.52 | 10.40 | 10.60 |
| Lys84 | 11.543 | 10.40 | 10.60 |
| Lys97 | 11.061 | 10.40 | 10.60 |
| Lys110 | 11.046 | 10.40 | 10.60 |
| Lys116 | 10.982 | 10.40 | 10.60 |
| Lys127 | 10.183 | 10.40 | 10.60 |
| Lys133 | 11.713 | 10.40 | 10.60 |
| Lys134 | 10.253 | 10.40 | 10.60 |
| Lys136 | 10.672 | 10.40 | 10.60 |
| Arg35 | 16.318 | 12.00 | 12.50 |
| Arg81 | 13.606 | 12.00 | 12.50 |
| Arg87 | 14.576 | 12.00 | 12.50 |
| Arg105 | 13.801 | 12.00 | 12.50 |
| Arg126 | 14.004 | 12.00 | 12.50 |
| Tyr27 | 12.44 | 10.00 | 9.80 |
| Tyr54 | 9.559 | 10.00 | 9.80 |
| Tyr85 | 8.284 | 10.00 | 9.80 |
| Tyr91 | 13.441 | 10.00 | 9.80 |
| Tyr93 | 14.705 | 10.00 | 9.80 |
| Tyr113 | 9.664 | 10.00 | 9.80 |
| Tyr115 | 10.177 | 10.00 | 9.80 |

Figure 2:
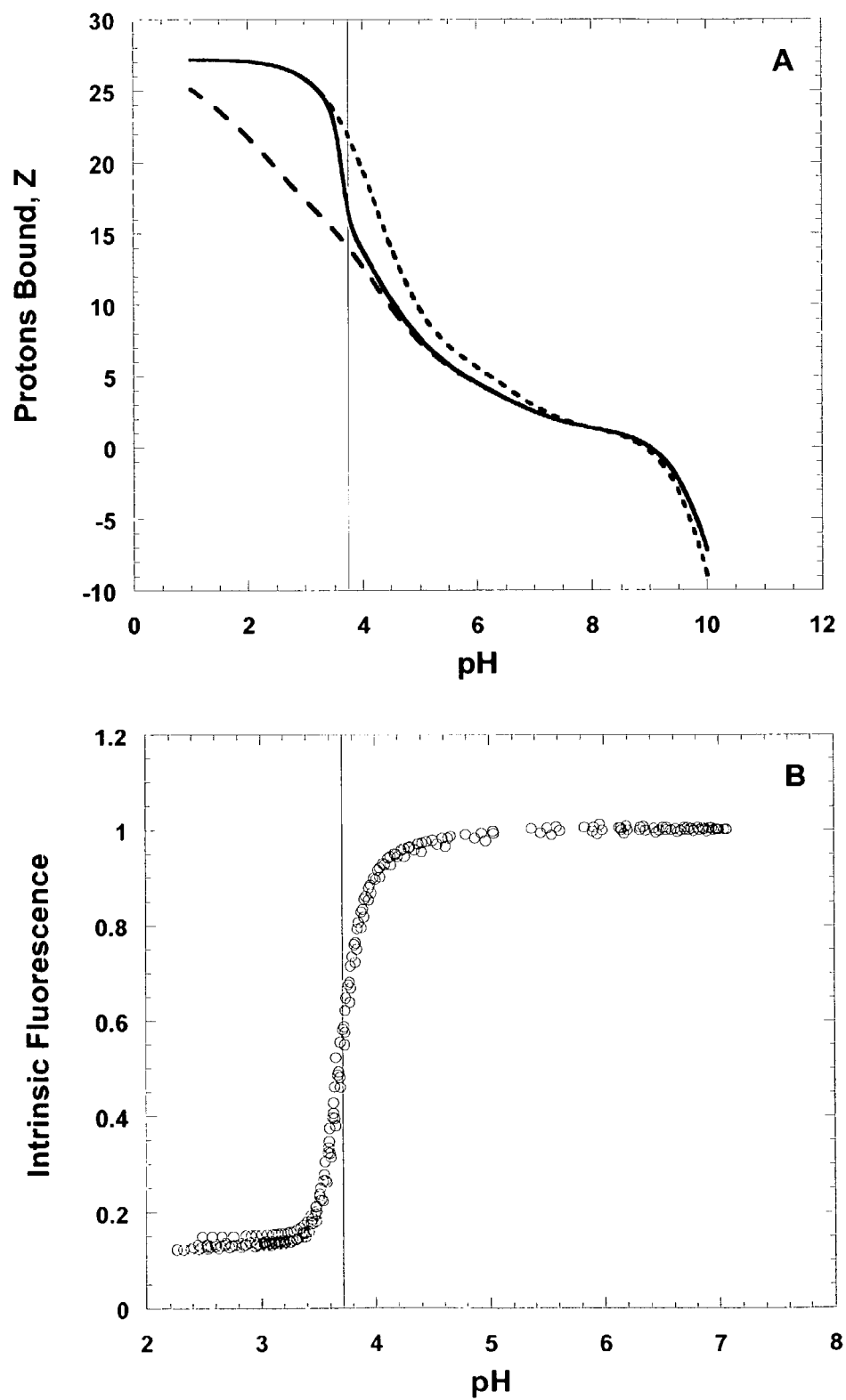
FIG. 2A and FIG. 2B show the proton titration of the SNase ensemble.

FIG. 2 showed the titration behavior using crystallographic pKa values (i.e. pKa,N values) calculated by FD solution of the linearized PB equation. pKa,N values calculated by FD solution of the non-linear PB equation yielded virtually identical pKa.

For comparison, proton titration of the fully folded and fully unfolded conformations of SNase were also shown in FIG. 2. The proton binding curve of the ensemble was be calculated by:

$$Z(pH)_{ensemble} = \sum_i Z(pH)_i * P(pH)_i \qquad (4)$$

where $Z(pH)_i$ was the number of protons bound to state i as a function of pH, and $P(pH)_i$ was the pH dependence of the population probability of state i, $P_i$, from equation $$P_i = \frac{\exp\left(\frac{-\Delta G_i}{RT}\right)}{Q}.$$

Thus, this calculation was shown in FIG. 2A along with numerical titration of the fully folded and fully unfolded states. It was evident from FIG. 2 that at near-neutral pH values, the ensemble had proton binding characteristics practically identical to the fully folded state. As the pH was decreased, the ensemble proton binding behavior rapidly shifted to that of the unfolded state. FIG. 2B demonstrated excellent agreement to the pH in which SNase is seen by experiment to shift from native to unfolded characteristics. The experimentally observed pH midpoint of the acid induced unfolding of SNase was 3.71 (Whitten et al., 2000). For comparison, a line was drawn through the plots in both FIG. 2A and FIG. 2B at this value of pH.

Yet further, experimentally, SNase was observed to have acid induced unfolding at pH 3.7 (Whitten et al., 2000). It was apparent from FIG. 2 that this computational technique accurately captured the acid-induced transition of this protein from native to unfolded characteristics.

Example 3

Titration Behavior

A. Prediction of Titration Behavior
To determine whether or not a titratable atom was protected from or exposed to solvent, the atom's solvent accessible surface area was calculated based on the Lee and Richards algorithm (Hilser et al., 1996; Lee et al., 1971; Murphy et al., 1992).

Figure 3:
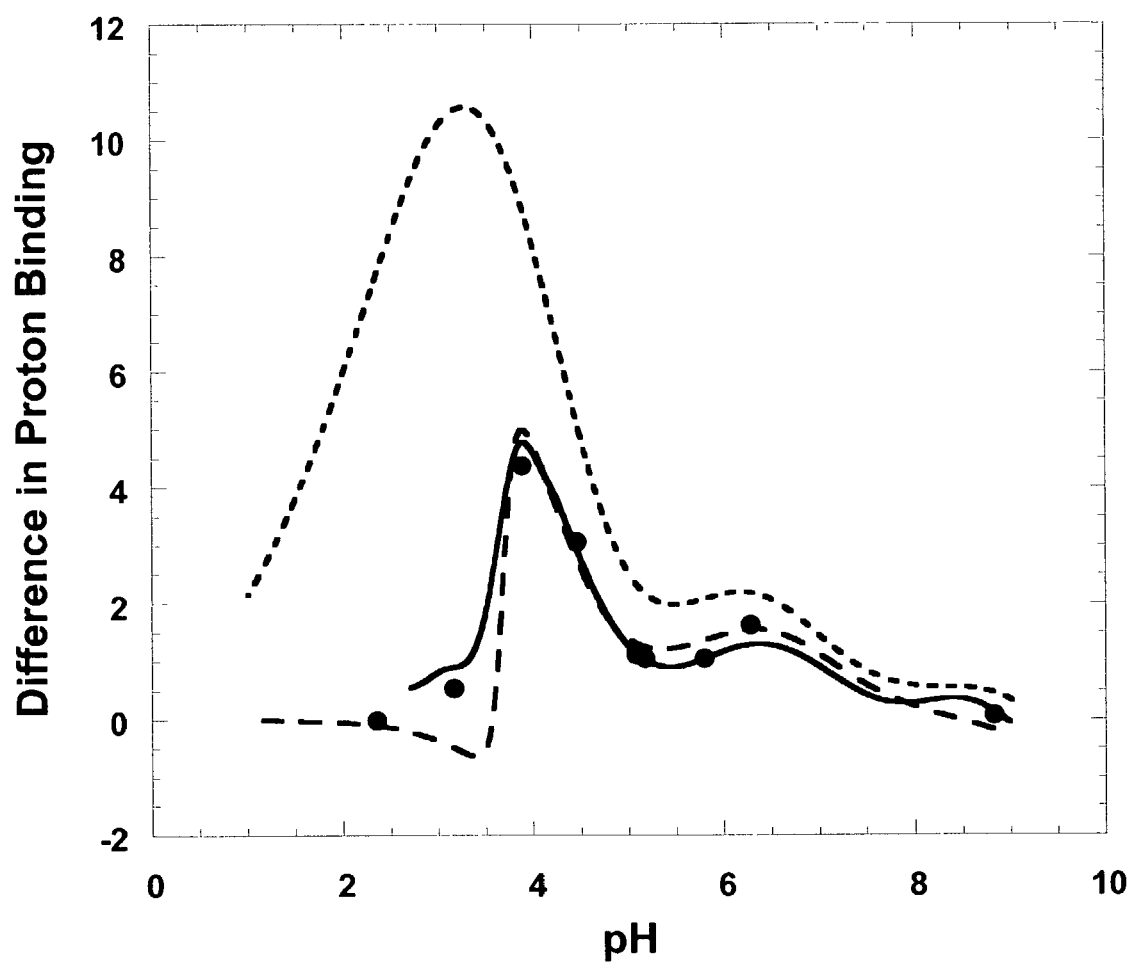
FIG. 3 shows the direct comparison of the predicted proton binding characteristics of the ensemble. Difference in proton binding observed between the fully unfolded state, using $pK_{a,GuHCl}$ values from Table 1, minus the native state that uses only the $pK_{a,protected}$ values (short dashes); the fully unfolded state, using $pK_{a,GuHCl}$ values, minus the ensemble (large dashes); and the experimentally measured difference in proton binding between SNase in 6 M GuHCl, 100 mM KCl, 20° C. and SNase in 100 mM KCl, 20° C. (solid line), (Whitten et al., 2000). Also shown are experimental batch measurements of the net number of protons bound by SNase due to unfolding induced by 6 M GuHCl at various pH (solid circles), (Whitten et al., 2000).

Briefly, this value was then divided by the maximum area of surface accessible to solvent for that atom type, determined by identical calculations on fully exposed models, to provide a percent exposed. If the percent exposed value was greater than a threshold percentage, the atom was modeled to titrate with its pK$_{a,exposed}$ value, else, the atom titrated with its pK$_{a,protected}$ value. The threshold percentage was determined by comparing the calculated proton binding curve to the experimentally observed proton binding curve (FIG. 3). A threshold percentage of 0.31 was used for the glutamic, aspartic, lysine, arginine and tyrosine residues; a value of 0.45 was used for the histidines. The solvent accessibilities of the OE1 and OE2 atoms were averaged for glutamic residues, the OD1 and OD2 atomic solvent accessibilities were averaged for aspartic residues, and the NH1 and NH2 solvent accessibilities were averaged for arginines. The solvent accessibility of the NE2 atom was used for histidines, the NZ for lysines, and the OH for tyrosines. There were no cysteine residues in SNase.

B. Experimentation of Titration Behavior
Titration of fully unfolded SNase in 6 M GuHCl was calculated by using the pKa values listed in Table 1. The difference in proton binding between the SNase ensemble and a fully unfolded GuHCl state was experimentally measured by two different methods. First, the "continuous difference curve" measured potentiometric titration of SNase under native conditions (e.g. 2 mg/ml SNase, 100 mM KCl, 298 K) and unfolding conditions (e.g. 2 mg/ml SNase, 6 M GuHCl, 100 mM KCl, 298 K) and then determined by the difference between these two curves (Whitten et al., 2000). Second, the "batch" technique determined the difference in proton binding between the ensemble and a fully unfolded GuHCl state at a specific pH (Whitten et al., 2000). Here, concentrated GuHCl was added to a solution of SNase under native conditions at a specific pH. The net number of protons bound or released at that pH due to the shift of the ensemble to fully unfolded GuHCl-induced states was calculated by the measured change in solution pH.

FIG. 3 demonstrated excellent agreement between the predicted ensemble titration behavior and that observed experimentally. Furthermore, FIG. 3 demonstrates that this ensemble-based approach also captured the highly cooperative nature of the acid-induced transition from native to unfolded ensemble characteristics, i.e. the net pick-up of approximately 5 protons due to acid-induced unfolding.

Example 4

Calculation of pH Dependence of the Ensemble's States

The pH dependence of the ensemble's population distribution of states was calculated by the linkage relationship (Wyman, 1948 and 1964):

$$\Delta G(\text{pH})_i = -2.303RT \int \Delta v(\text{pH})_i d\text{pH} + \Delta G_{COREX,i} \quad (5)$$

where $\Delta G\text{pH},i$ was the pH dependence of stability of state i relative to the "native" crystallographic structure (N), R was the gas constant, T was temperature, $\Delta v\text{pH},i$ was the difference in proton binding between state i and N as a function of pH, and $\Delta G_{COREX,i}$ was the stability of state i determined by empirical parameterization of the intrinsic energetics ($\Delta G$, $\Delta H$, and $\Delta S$) through solvent accessible surface area calculations as stated above. Thus, with respect to Asp 21, decreasing pH shifted the equilibrium distribution of states to the second and third sub-ensembles in FIG. 1 at the expense of population of the states in the first sub-ensemble (i.e. Asp 21 had a higher affinity for protons in sub-ensembles 2 and 3 relative to sub-ensemble 1).

FIG. 1 also showed 10 of the more stable states for each of three sub-ensembles generated by COREX. The white arrow showed the position of residue Asp 21. Folded regions are indicated by dark gray and light gray represented unfolded regions.

In all states of the first sub-ensemble, Asp 21 was folded and protected from solvent and titrated with its crystallographic pKa (pKa,N=0.524 by FD/PB calculations assuming an ionic strength of 100 mM).

In the second sub-ensemble, Asp 21 was folded but exposed to solvent and titrated with a pKa of 4.0. In the third sub-ensemble, Asp 21 was unfolded, thus exposed to solvent and also titrated with a pKa of 4.0 in these states.

With respect solely to Asp21, it was shown that decreasing pH shifted the equilibrium population of states to the second and third sub-ensembles at the expense of the states in the first sub-ensemble.

A similar representation and argument was made for each titratable residue of the protein. Following this reasoning, the cooperativity of any pH induced shift in ensemble population was linked to the overlap in the residue specific sub-ensembles imitated in FIG. 1.

Example 4

Calculation of pH Dependence of the Specific Residues

The present invention predicted the residue-specific contributions to the pH dependent stability of a protein.

All residues did not equally affect stability upon titration; some titratable groups were fully exposed to solvent, contributing to stability mainly through solubility concerns, and any possible intramolecular coulombic interactions were attenuated by the ionic and polar components of the solvent; other titratable groups participated in substantial intramolecular coulombic interactions, minimally attenuated by the solvent, and contributed substantially to the electrostatic and proton-linked components of protein stability.

For each state of the ensemble, a specific residue titrated with the crystallographic pKa value (pKa,N) if the titratable atom of the residue was protected from solvent in that state. If the titratable atom was exposed to solvent, the residue titrated with the pKa values given in Table 1, based on solvent exposed model compounds (Schaefer et al., 1998; Matthew et al., 1985).

Figure 4A:
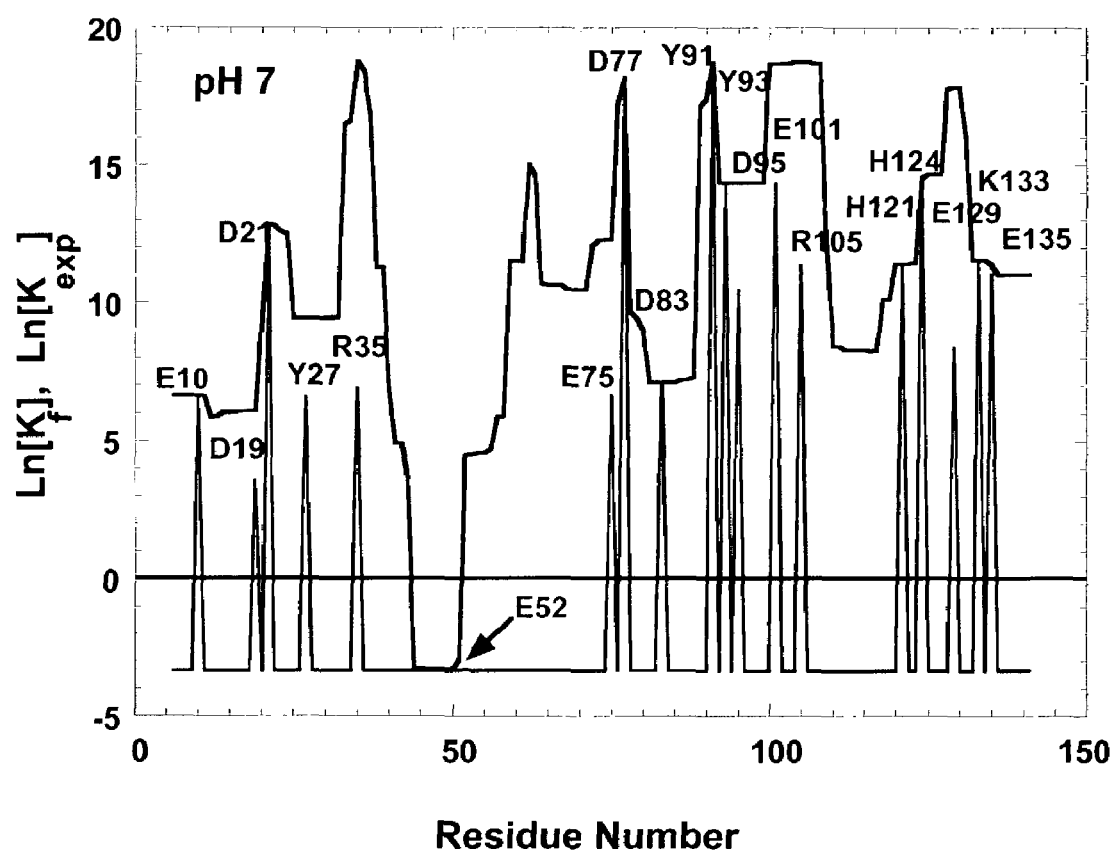
FIG. 4A and FIG. 4B shows the Ln[Kf] and Ln[K exp] and the ΔΔ GpH 7.

FIG. 4A presented two key metrics of a titratable residue's contribution to the pH dependent stability of the protein. The probability that a given residue j was in the folded conformation, $P_{folded,j}$, was equal to the sum of the probabilities of all the conformational states of the protein in which residue j resided in a folded region. Likewise, the probability that residue j was unfolded, $P_{unfolded,j}$, was equal to the sum of the probabilities of all the conformational states of the protein in which residue j resided in an unfolded region. The apparent folding constant per residue, $K_{folded,j}$, was thus defined as the ratio of probabilities of all states in which residue j was folded to the probabilities of the states in which residue j was not folded.

$$K_{folded,j} = \frac{P_{folded,j}}{P_{unfolded,j}} \quad (6)$$

Similarly, an apparent protection constant per residue, $K_{protected,j}$, was defined as the ratio of the sum of the probabilities of all states in which the titratable atom of residue j was protected from solvent to the sum of the probabilities of all states in which the titratable atom of residue j was exposed.

$$K_{folded,j} = \frac{P_{protected,j}}{P_{exposed,j}} \quad (7)$$

FIG. 4A showed the residues that possessed a high probability of being both folded and protected from solvent. These residues were thus predicted to be the dominant contributors to the pH dependence of stability of SNase. Residues that resided in regions of the protein with little probability of being folded did not contribute to the pH dependent stability even if they possessed $pK_a$ shifted from $pK_{a,exposed}$ values and were protected from the solvent in the fully folded state. Glu52 was such an example; a residue that by the crystal structure itself was predicted to contribute significantly to the pH dependent stability of SNase, owing to a p$K_a$ depressed by approximately 2.5 pK units. Similarly, residues with little probability of being protected from solvent also did not contribute to the pH dependent stability regardless of whether or not they had high probabilities of being folded; an example was Glu73.

FIG. 5A–FIG. 5D also showed the different ensemble titration behavior of other residues. The pH dependent ensemble equilibrium dramatically increased the cooperativity of the proton binding reaction for some residues but not all.

Example 6

Experimental Analysis of SNase

It's difficult to predict the effect on the stability of a protein of the substitution of one amino acid for another; this was the major difficulty of mutational analysis of proteins. However, FIG. 4A predicted that removal of the titratable capabilities of the residues significantly altered the pH dependent energetics of SNase.

To test this prediction, a library of SNase point mutants was obtained. In each mutant, a histidine, glutamic, and aspartic residue in SNase was substituted to alanine. The effect of these point mutations on the stability and pH midpoint of acid induced unfolding was shown in FIG. 4B.

SNase, wild type and mutant forms, was expressed and purified following the procedure (Shortle et al., 1989). The purity of the protein was established to be >98% by SDS-PAGE. Protein concentrations were determined at 280 nm using an optical density of 0.93.

Acid induced unfolding of SNase, performed at 20° C., was monitored by the intrinsic fluorescence of Trp-140 to obtain the pH midpoint of the unfolding transition (Whitten et al., 2000).

SNase stability, wild type and mutant forms, was determined by GuHCl induced unfolding, performed at pH 7 and 20° C., as monitored by the intrinsic fluorescence of Trp-140 (Whitten et al., 2000). The difference in stability between wild type and each mutant, $\Delta\Delta G(pH7)$, was calculated by:

$$\Delta\Delta G(pH7) = \Delta G(pH7)_{mu\,tan\,t} - \Delta G(pH7)_{wt} \qquad (8)$$

Figure 4B:
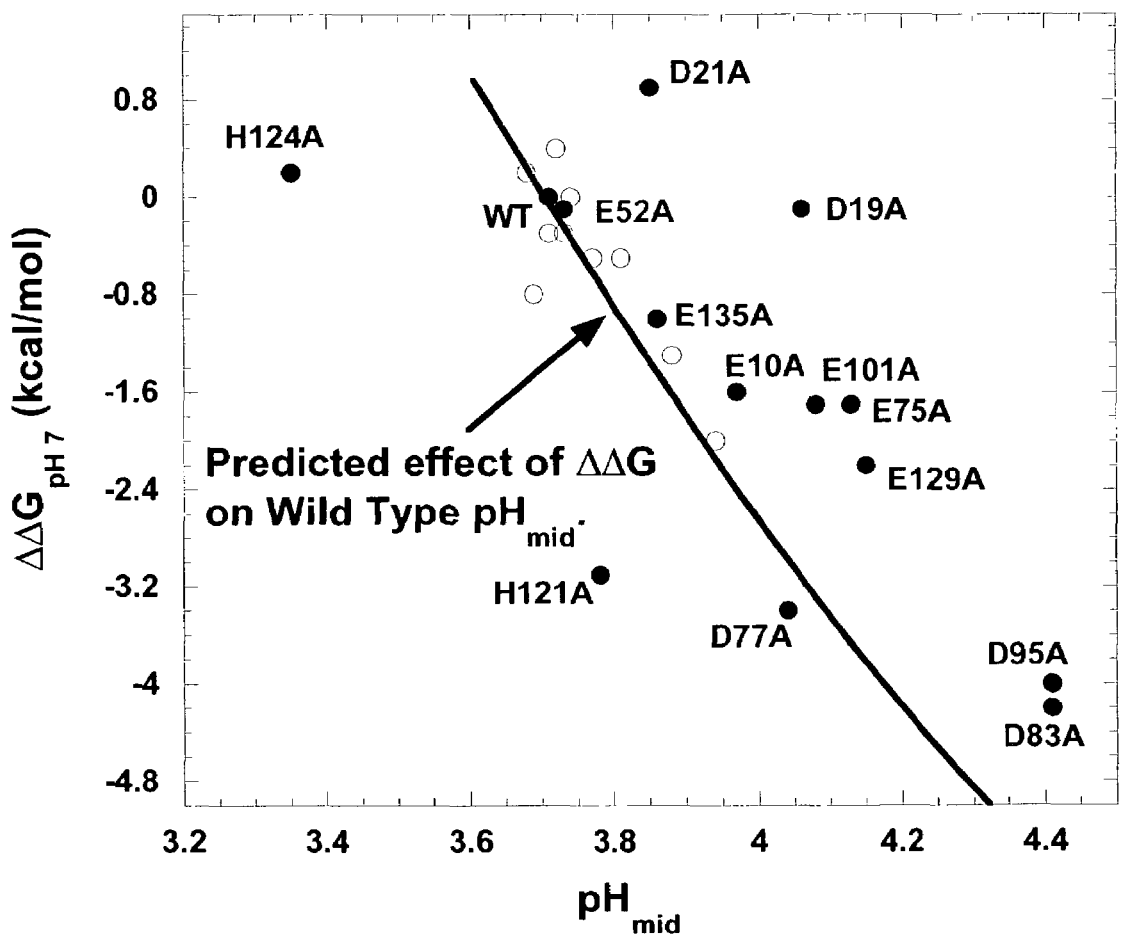
Figure 5A:
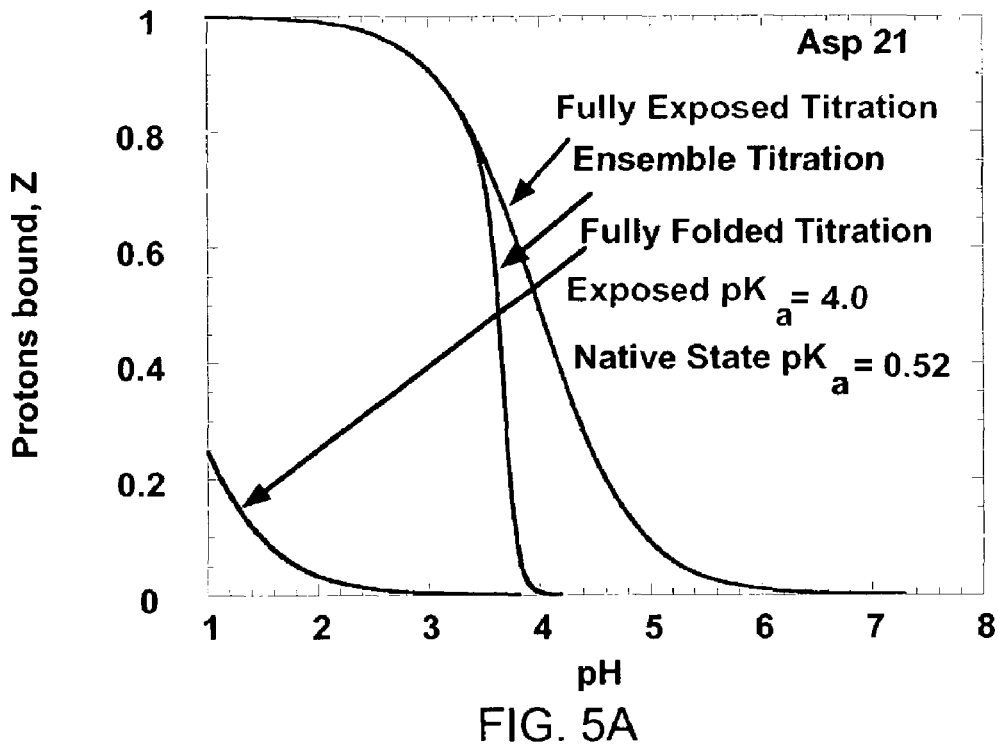
FIG. 5A–FIG. 5D show the different ensemble titration behavior of the residues, Glu52, Asp21 and Asp19.
Figure 5B:
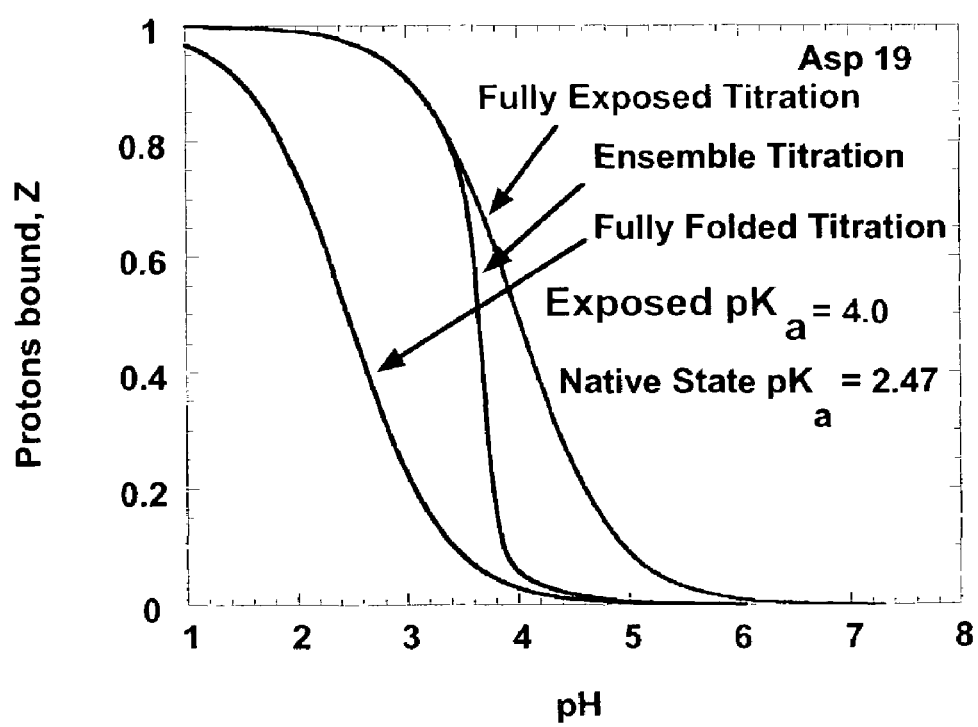
Figure 5C:
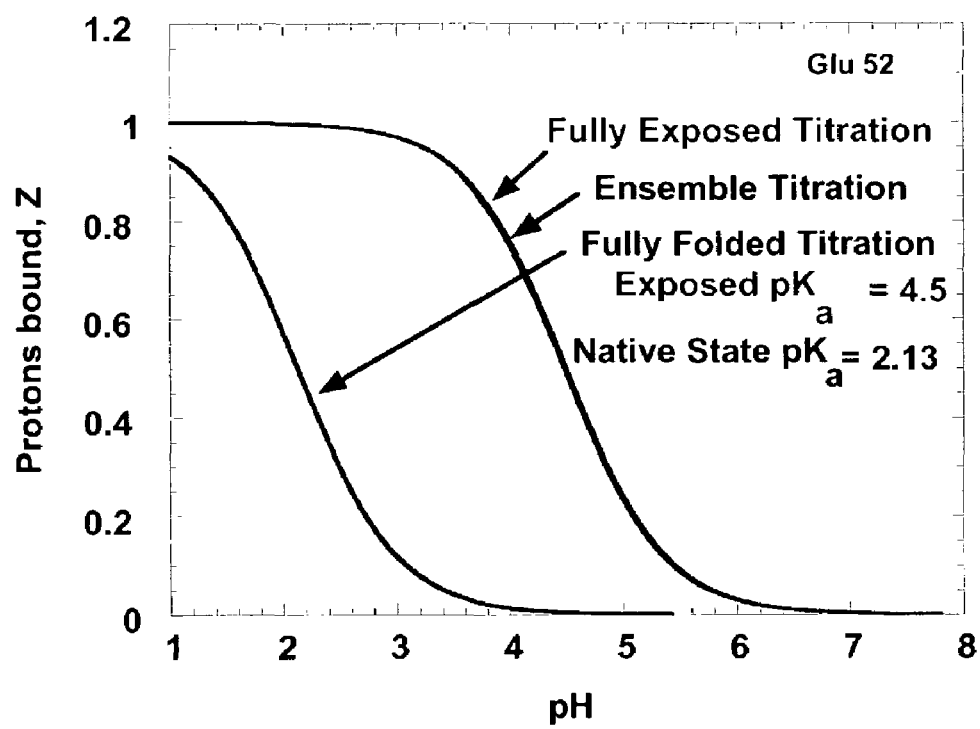
Figure 5D:
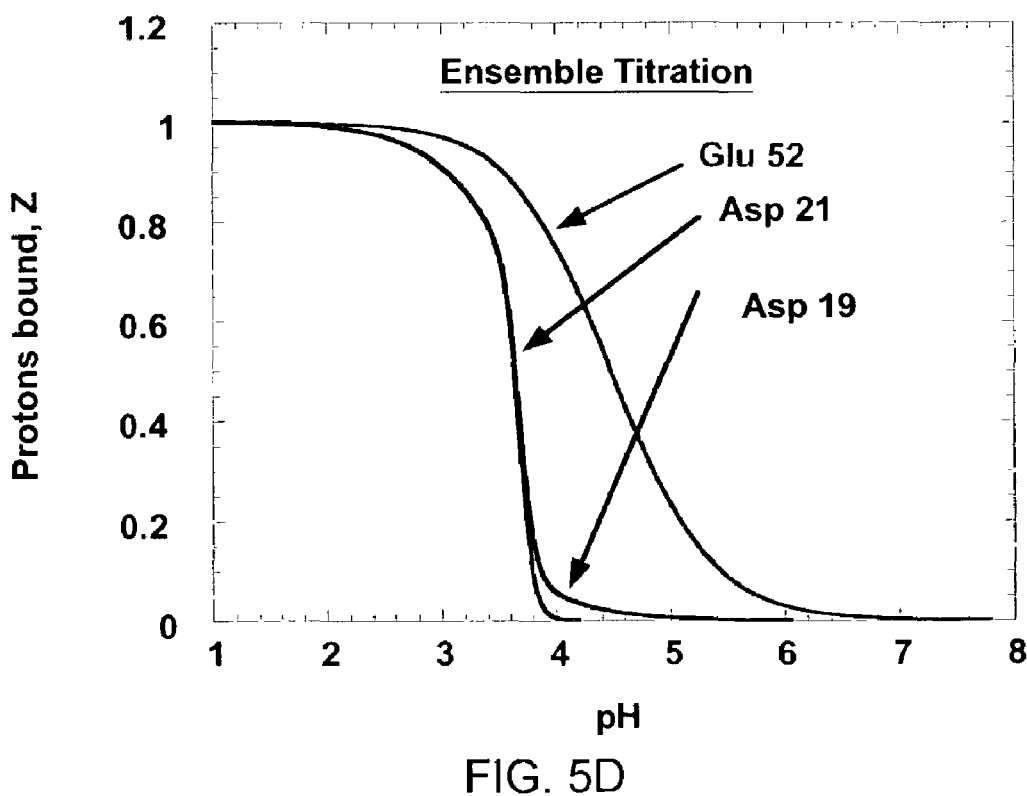

Point mutations in FIG. 4B corresponded to the residues in FIG. 4A. Computationally, the effect of changes in stability on the pH midpoint of acid denaturation of wild type SNase was predicted by the first term of equation 4 and using the difference in proton binding between the fully unfolded state and the ensemble for the value of $\Delta v(pH)_i$. Results of this calculation were also shown in FIG. 4B. Mutations that substituted a residue for alanine were off the predicted curve of FIG. 4B as this substitution was predicted to eliminate titration of a residue that contributed to the pH dependent stability of SNase and therefore to $\Delta v(pH)_i$. The correlation of FIG. 4A and FIG. 4B demonstrated the ability of this method to accurately predict which residues of the protein were critical to its pH dependent stability.

REFERENCES

All patents and publications mentioned in the specification are indicative of the level of those skilled in the art to which the invention pertains. All patents and publications are herein incorporated by reference to the same extent as if each individual publication was specifically and individually indicated to be incorporated by reference.

U.S. Pat. No. 4,554,101
U.S. Pat. No. 5,446,128
U.S. Pat. No. 5,440,013
U.S. Pat. No. 5,475,085
U.S. Pat. No. 5,618,914
U.S. Pat. No. 5,635,377
U.S. Pat. No. 5,670,155
U.S. Pat. No. 5,672,681
U.S. Pat. No. 5,674,976
U.S. Pat. No. 5,710,245
U.S. Pat. No. 5,789,166
U.S. Pat. No. 5,840,833
U.S. Pat. No. 5,859,184
Alberts et al. (1994) *Molecular Biology of the Cell* p 57.
Antosiewicz J. et al., (1994) *J. Mol. Biol.* 238:415.
Bai Y. et al., (1995) *Science* 269:192.
Baldwin R. L. 1986. *Proc Natl Acad Sci USA* 83: 8069–8072.
D'Aquino J. A. et al., (1996) *Proteins: Struct. Funct. Genet.* 25:143.
Englander S. W. (2000) *Annu. Rev. Biophys. Biomol. Struct.* 29:213.
Freire E. and Biltonen R. L. (1978) *Biopolymers* 17:463.
Freire E. (1998) *Adv.Protein Chem.* 51:255.
Freire E. (1999) *Proc. Nat. Acad. Sci. USA* 96:10118.
Gomez J. and Freire E. (1995) *J. Mol. Biol.* 252:337.
Gomez J. et al., (1995) *Proteins: Struct. Funct. Genet.* 22:404.
Habermann S. M. and Murphy K. P. 1996. *Prot Sci* 5: 1229–1239.
Hilser V. J. and Freire E. (1996) *J. Mol. Biol.* 262:756.
Hilser V. J. et al., (1998) *Proc. Nat. Acad. Sci. USA* 95:9903.
Hilser V. J. (1997) *Biophys. Chem.* 64:69.
Jayaram B. et al., (1989) *Biopolymers* 28:975.
Johannesson et al., 1999, *J. Med. Chem.* 42:601–608.
Johnson M. S. et al., (1993) *J Mol Biol.* 231(3):735–52.
Kim P. S. and Baldwin R. L. (1990) *Annu. Rev. Biochem.* 59:631.
Klapper I. et al., (1986) *Proteins* 1:47.
Kuwajima K. (1989) *Proteins: Struct. Funct. Genet.* 6:87.
Lee B. and Richards F M. (1971) *J. Mol. Biol.* 55:379.
Lee K. H. et al., 1994. *Proteins* 20: 68–84.
Matthew J. B. and Gurd F. R. (1986) *Methods Enzymol.* 130:413.
Matthew J. B. et al., (1985) *CRC Crit. Rev. Biochem.* 18:91.
Mayne L. and Englander S. W. (2000) *Protein Science* 9:1873.
Milne J. S. et al., (1999) *J. Mol. Biol.* 290:811.
Murphy K. P. et al., (1992). *J. Mol. Biol.* 227:293.
Nozaki Y. and Tanford C. (1967) *J. Am. Chem. Soc.* 89:736.
Pan H. et al., (2000) *Proc. Nat. Acad. Sci. USA* 97:12020.
Roxby R, and Tanford C. (1971) *Biochemistry* 10:3348.
Schaefer M. et al., (1998) *Adv. Protein Chem.* 51:1.
Shortle D. and Meeker A. K. (1989) *Biochemistry* 28:936.
Tanford C. (1962) *Adv. Protein Chem.* 27:69.
Tanford C. (1969) *Adv. Protein Chem.* 24:1.
Tanford C. and Kirkwood J. G. (1957) *J. Am. Chem. Soc.* 79:5333.
Vita et al., 1998, *Biopolymers* 47:93–100.
Warwicker J. (1986) *J. Theor. Biol.* 121:199.
Weisshoff et al., 1999, *Eur. J. Biochem.* 259:776–788.
Whitten S. T. and Garcia-Moreno E. B. (2000) *Biochem.* 39:14292
Wooll J. O. et al., (2000) *J. Mol. Biol.* 301:247.
Xie D. and Freire E. (1994) *J. Mol. Biol.* 242:62.
Xie D. and Freire E. (1994) *Proteins: Struct. Funct. Genet.* 19:291.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method of predicting the macroscopic $pK_a$ of a protein comprising the steps of:
    generating an ensemble of incrementally different conformational states by combinatorial unfolding of a set of predefined folding units in all possible combinations of each protein;
    determining the probability of each said conformational state;
    calculating the pH dependence of each said conformational state; and
    predicting the macroscopic pKa of the protein comprising determining the pH dependence of the proton binding using the equation $$Z(pH)_{ensemble} = \sum_i Z(pH)_i * P(pH)_i.$$

2. The method of claim 1, wherein the $pK_a$ determines the solubility of the protein.

3. A method of calculating the macroscopic $pK_a$ of a protein comprising the steps of:
    generating an ensemble of incrementally different conformational states by combinatorial unfolding of a set of predefined folding units in all possible combinations of each protein; and
    calculating a proton binding curve of the ensemble using the equation $$Z(pH)_{ensemble} = \sum_i Z(pH)_i * P(pH)_i.$$

4. A computer system for calculating the macroscopic $pK_a$ of a protein comprising:
    a database containing pH dependence data for a protein; and
    a software program coupled with said database, the software program adapted for performing the steps of:
        generating an ensemble of incrementally different conformational states by combinatorial unfolding of a set of predefined folding units in all possible combinations of each protein; and
        calculating a proton binding curve of the ensemble using the equation $$Z(pH)_{ensemble} = \sum_i Z(pH)_i * P(pH)_i.$$

5. A computer-readable medium having computer-executable instructions for performing the steps recited in claim 3.

6. A computer-readable medium having computer-executable instructions for performing the steps recited in claim 4.

7. A computer-readable medium having computer-executable instructions for performing the steps recited in claim 1.

8. The method of claim 1, wherein the generating step comprises dividing the proteins into folding units by placing a block of windows over the entire sequence of the protein and sliding the block of windows one residue at a time.

9. The method of claim 1, wherein the determining step comprises calculating the free energy of each of the conformational states in the ensemble; determining the Boltzmann weight $[K_i = \exp(-\Delta G_i/RT)]$ of each state; and determining the probability of each state using the equation $$P_i = \frac{K_i}{\sum K_i'}.$$

10. The method of claim 1, wherein the calculating step comprises determining the linkage relationship of the pH dependence of stability of all microscopic states using the equation $$\Delta G(pH)_i = -2.303 RT \int \Delta v(pH)_i dpH + \Delta G_{COREX,i}.$$

11. The method of claim 1 further comprising predicting the residue-specific contributions to the pH dependent stability of the protein comprising the step of determining the ratio of probabilities of all microscopic states using the equation $$K_{folded,j} = \frac{P_{folded,j}}{P_{unfolded,j}}.$$

12. The method of claim 1 further comprising predicting the protection constant per residue of the protein comprising the step of determining the sum of the probabilities of all microscopic states in which a residue is exposed using the equation $$\text{and } K_{folded,j} = \frac{P_{protected,j}}{P_{exposed,j}}.$$

* * * * *